United States Patent
Kubanek et al.

(10) Patent No.: US 9,505,705 B2
(45) Date of Patent: Nov. 29, 2016

(54) METHOD FOR PRODUCING AMINES WITH A CATALYST CONTAINING PLATINUM, NICKEL AND AN ADDITIONAL METAL

(75) Inventors: Petr Kubanek, Mannheim (DE); Ekkehard Schwab, Neustadt (DE); Frederik van Laar, Dubai (AE); Wolfgang Mackenroth, Bad Duerkheim (DE)

(73) Assignee: BASF AKTEINGESELLSCHAFT, Ludwigshafen (DE)

( * ) Notice: Subject to any disclaimer, the term of this patent is extended or adjusted under 35 U.S.C. 154(b) by 1198 days.

(21) Appl. No.: 12/065,285

(22) PCT Filed: Aug. 21, 2006

(86) PCT No.: PCT/EP2006/065478
§ 371 (c)(1),
(2), (4) Date: Feb. 29, 2008

(87) PCT Pub. No.: WO2007/025884
PCT Pub. Date: Mar. 8, 2007

(65) Prior Publication Data
US 2008/0242537 A1    Oct. 2, 2008

(30) Foreign Application Priority Data
Aug. 31, 2005  (DE) .................. 10 2005 041 532

(51) Int. Cl.
| | | |
|---|---|---|
| *C07C 209/36* | (2006.01) | |
| *B01J 21/18* | (2006.01) | |
| *B01J 23/89* | (2006.01) | |
| *B01J 37/02* | (2006.01) | |
| *B01J 37/16* | (2006.01) | |

(52) U.S. Cl.
CPC .............. *C07C 209/36* (2013.01); *B01J 21/18* (2013.01); *B01J 23/892* (2013.01); *B01J 23/8953* (2013.01); *B01J 37/0201* (2013.01); *B01J 37/16* (2013.01); *Y02P 20/52* (2015.11)

(58) Field of Classification Search
CPC ..................................................... C07C 209/36
See application file for complete search history.

(56) References Cited

U.S. PATENT DOCUMENTS

| | | | |
|---|---|---|---|
| 2,894,036 A | * | 7/1959 | Graham ................ C07C 209/36 534/566 |
| 3,127,356 A | | 3/1964 | Hamilton et al. |
| 4,185,036 A | | 1/1980 | Cossaboon |
| 4,298,462 A | | 11/1981 | Antos |
| 4,374,046 A | | 2/1983 | Antos |
| 4,743,577 A | * | 5/1988 | Schroeder et al. ........... 502/326 |
| 5,120,875 A | * | 6/1992 | Birkenstock et al. ........ 564/417 |
| 5,214,212 A | | 5/1993 | Whitman |
| 7,468,461 B2 | * | 12/2008 | Van Laar et al. ............. 564/423 |
| 2002/0077504 A1 | * | 6/2002 | Albers ..................... B01J 21/18 564/423 |
| 2003/0207761 A1 | * | 11/2003 | Ding ............................ 502/326 |
| 2004/0199017 A1 | | 10/2004 | Ding |
| 2005/0227128 A1 | | 10/2005 | Devenney et al. |
| 2007/0149814 A1 | | 6/2007 | Van Laar |
| 2010/0130788 A1 | * | 5/2010 | Coelho Tsou et al. ....... 564/422 |

FOREIGN PATENT DOCUMENTS

| | | | | |
|---|---|---|---|---|
| DE | 39 28 329 | | 2/1991 | |
| DE | 196 36 214 | | 1/1998 | |
| DE | 199 11 865 | | 9/2000 | |
| DE | WO2005037768 | * | 4/2005 | ........... C07C 209/36 |
| EP | 0 124 010 | | 11/1984 | |
| EP | 0 415 158 A2 | | 3/1991 | |
| EP | 0 415 158 A3 | | 3/1991 | |
| EP | 0 595 124 | | 5/1994 | |
| EP | 768 917 | | 4/1997 | |
| EP | 1 358 935 | | 11/2003 | |
| WO | 03 039743 | | 5/2003 | |

OTHER PUBLICATIONS

Fundamentals of Chemistry 3rd edition by Brady and Holum (1988).*

* cited by examiner

*Primary Examiner* — Clinton Brooks
(74) *Attorney, Agent, or Firm* — Oblon, McClelland, Maier & Neustadt, L.L.P.

(57) ABSTRACT

The invention provides a process for preparing aromatic amines by catalytically hydrogenating the corresponding nitro compounds, especially for preparing tolylenediamine by hydrogenating dinitrotoluene, which comprises using hydrogenation catalysts in which the active component present is a mixture of platinum, nickel and an additional metal on a support.

13 Claims, No Drawings

METHOD FOR PRODUCING AMINES WITH A CATALYST CONTAINING PLATINUM, NICKEL AND AN ADDITIONAL METAL

The invention relates to a process for preparing amines by catalytically hydrogenating the corresponding nitro compounds, and also novel catalysts for carrying out the process.

The preparation of amines, in particular of aromatic mono-, di- and/or polyamines, by catalytically hydrogenating the corresponding mono-, di- and/or polynitro compounds has been known for some time and is described many times in the literature. An aromatic amine which is frequently used in industry is tolylenediamine (TDA) which may be further processed to tolylene diisocyanate and is prepared by hydrogenating dinitrotoluene (DNT). A problem in the hydrogenation of DNT is the increased formation of by-products; in addition to low boilers, usually deaminated and ring-hydrogenated products, high molecular weight or tarlike products frequently occur and not only reduce the yield of the process but may also lead to premature deactivation of the catalyst.

Useful hydrogenation catalysts, as described, for example, in EP-A-0 124 010, are frequently metals of transition group VIII of the Periodic Table, in particular Raney iron, Raney cobalt and Raney nickel.

Frequently, catalysts are also used for the hydrogenation of nitroaromatics and comprise noble metals, in particular palladium, or else platinum. Also known in this context are catalysts which comprise platinum and nickel.

For instance, U.S. Pat. No. 3,127,356 describes a process for preparing hydrogenation catalysts for the hydrogenation of DNT to TDA. The catalysts comprise a support, an oleophilic hydrocarbon component, for example carbon black, to which the metals are applied. In this case, the nickel is present in the catalyst as the oxide or hydroxide.

U.S. Pat. No. 5,214,212 describes a process for ring-hydrogenating aromatic amines. The catalyst used is a noble metal catalyst which may additionally be doped with further metals, including nickel. The noble metal used may be platinum in a mixture with other noble metals. The noble metals are present in the catalyst as metals and the doped metals in the form of salts.

DE 39 28 329 describes a process for preparing chlorine-substituted aromatic amines from the corresponding nitro compounds. The catalyst used in this process consists of activated carbon as a support, to which platinum and a further metal, in particular nickel, are applied.

EP 595 124 describes a process for preparing chlorine-substituted aromatic amines from the corresponding nitro compounds. The catalyst used comprises platinum and nickel on activated carbon. In this process, platinum is initially applied to the activated carbon and reduced and then nickel is applied to the support in the form of a salt. The nickel is present in this catalyst as the hydroxide.

EP 768 917 describes a catalyst for preparing carboxylic acid salts. This consists of an anchor metal, for example platinum, some of which is embedded in an alkali-resistant support, and at least some of which has been coated by electroless deposition with a catalytically active non-noble metal, for example nickel. In this catalyst, the two metals are present on the support as separate phases.

US 2004/0199017 A1 describes a monolithic catalyst for hydrogenating dinitrotoluene to tolyldiamine. This consists of a monolithic support with aluminum oxide coating layer; the active components described are palladium, nickel and a promoter, for example zinc, cadmium, copper or silver.

U.S. Pat. No. 4,185,036 describes a process for hydrogenating mixtures of nitroaromatics. The catalysts used comprise platinum and, if appropriate, a further metal, for example nickel, on activated carbon. The further metal is present in the form of the oxide or hydroxide on the support.

DE 199 11 865 and DE 196 36 214 describe processes for hydrogenating dinitrotoluene. The catalysts used comprise iridium and also at least one doping element, for example nickel or platinum.

WO 03/39743 describes a process for preparing TDA using a hydrogenation catalyst consisting of platinum, a further noble metal and a non-noble metal.

WO 05/037768 describes catalysts and processes for hydrogenating dinitrotoluene to tolyldiamine. The catalysts consist of platinum and nickel, the two metals being present in the form of an alloy on the support.

It is an ever-present object when hydrogenating DNT to TDA to further increase the yield and in particular to improve the selectivity of the process, in order thus to suppress the side reactions which lead to the formation of high molecular weight by-products or to the formation of low boilers. In addition, the catalyst should be stable even at relatively high reaction temperatures and not permit any deterioration in the selectivity of the process.

In order to conduct an economically viable process, the preparation and workup of the catalyst have to be at minimum cost. The preparation of the catalyst becomes cheaper when it is carried out in a minimum number of preparation steps. The workup of spent noble metal catalysts becomes cheaper when the fraction of additional base metal components is minimized.

It is an object of the present invention to provide catalysts for the hydrogenation of aromatic nitro compounds to the corresponding amines, in particular of DNT to TDA, which lead to a higher yield and selectivity of the process and whose preparation and workup is associated with low costs.

Surprisingly, this object is achieved by the use of hydrogenation catalysts consisting of platinum, nickel and an additional element on a support in the hydrogenation of aromatic nitro compounds to the corresponding amines.

The present invention thus provides processes for preparing aromatic amines by catalytically hydrogenating the corresponding nitro compounds, especially for preparing tolylenediamine by hydrogenating dinitrotoluene, which comprises using hydrogenation catalysts in which the active component present is a mixture of platinum, nickel and an additional metal on a support.

The invention further provides catalysts for preparing aromatic amines by catalytically hydrogenating the corresponding nitro compounds, especially for preparing tolylenediamine by hydrogenating dinitrotoluene, wherein the hydrogenation catalysts comprise, as an active component, a mixture of platinum, nickel and an additional metal on a support.

The invention further provides for the use of hydrogenation catalysts comprising, as an active component, a mixture of platinum, nickel and an additional metal on a support for preparing aromatic amines by catalytically hydrogenating the corresponding nitro compounds, especially for preparing tolylenediamine by hydrogenating dinitrotoluene.

The additional metal is preferably selected from the group comprising copper, cobalt, iron, zinc, manganese and chromium, especially from the group comprising copper, cobalt, iron and zinc.

The metal particles are usually polycrystalline, and may be characterized with a high-resolution TEM (FEG-TEM: Field Emission Gun-Transmission Electron Microscopy).

The support used for the catalysts may be the customary and known materials for this purpose. Preference is given to using activated carbon, carbon black, graphite or metal oxides, preferably hydrothermally stable metal oxides, for example $ZrO_2$, $TiO_2$. In the case of graphite, particular preference is given to HSAG (high surface area graphite) having a surface area of from 50 to 300 $m^2/g$. Particular preference is given to activated carbons, especially the physically or chemically activated activated carbons, or carbon blacks such as acetylene black.

The inventive hydrogenation catalysts comprise preferably 1-5% by weight of platinum, from 0.3 to 1.5% by weight of nickel and 0.05-1.5% by weight of the additional element, based in each case on the weight of the catalyst. The content of base metals is preferably not more than 1.6% by weight, in particular not more than 0.9% by weight, based in each case on the weight of the catalyst.

In the performance of the hydrogenation process according to the invention, the inventive catalyst is preferably used in an amount of from 0.01 to 10% by weight, more preferably from 0.01 to 5% by weight, in particular from 0.2 to 2% by weight, based on the reaction mixture.

The catalyst is usually introduced into the reactor in the reduced and passivated state. The reduced and passivated state of the catalyst means that the catalyst has been activated after the preparation, but, for safety reasons, the active centers have been passivated, for example by passing over oxygen or carbon dioxide. Alternatively, the catalyst may be conditioned and stabilized under an inert atmosphere or in a nonflammable solvent, for example in water, TDA/water or higher alcohols such as butanol or ethylene glycol.

The process according to the invention may be carried out continuously or batchwise using customary reactors with customary process parameters such as pressure and temperature.

Preference is given to carrying out the process for preparing aromatic amines, especially DNT, using inventive catalysts at pressures in the range from 5 to 100 bar, more preferably from 10 to 40 bar, in particular from 20 to 25 bar.

Preference is given to carrying out the process for preparing aromatic amines, especially DNT, using inventive catalysts according to the invention at a temperature in the range from 80 to 250° C., more preferably in the range from 100 to 220° C. and in particular in the range from 160 to 200° C.

Usually, the hydrogenation is carried out in the form of a continuous suspension hydrogenation in customary and suitable reactors. Useful reactors are, for example, stirred tanks or loop reactors, for example jet-loop reactors, loop Venturi reactors, or loop reactors having internal flow circulation, as described in WO 00/35852. To remove the catalysts from the discharged reaction mixture, for example, crossflow filters may be used. Such a process is described, for example, in WO 03/66571.

The amines formed in the hydrogenation are removed continuously or batchwise from the hydrogenation procedure and subjected to a workup, for example a distillative aftertreatment.

Preference is given in the process according to the invention to using aromatic nitro compounds having one or more nitro groups and from 6 to 18 carbon atoms, for example nitrobenzenes, e.g. o-, m-, p-nitrobenzene, 1,3-dinitrobenzene, nitrotoluenes, e.g. 2,4-, 2,6-dinitrotoluene, 2,4,6-trinitrotoluene, nitroxylenes, e.g. 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes, e.g. 1-, 2-nitronaphthalene, 1,5- and 1,8-dinitro-naphthalene, chloronitrobenzenes, e.g. 2-chloro-1,3-, 1-chloro-2,4-dinitrobenzene, o-, m-, p-chloronitrobenzene, 1,2-dichloro-4-, 1,4-dichloro-2-, 2,4-dichloro-1- and 1,2-dichloro-3-nitrobenzene, chloronitrotoluenes, e.g. 4-chloro-2-, 4-chloro-3-, 2-chloro-4- and 2-chloro-6-nitrotoluene, nitroanilines, e.g. o-, m-, p-nitroaniline; nitroalcohols, e.g. tris(hydroxymethyl)nitromethane, 2-nitro-2-methyl-, 2-nitro-2-ethyl-1,3-propanediol, 2-nitro-1-butanol and 2-nitro-2-methyl-1-propanol, and also any mixtures of two or more of the nitro compounds mentioned.

Preference is given to using the process according to the invention to hydrogenate aromatic nitro compounds, preferably mononitrobenzene, methylnitrobenzene or methylnitrotoluene, and in particular 2,4-dinitrotoluene or its technical mixtures with 2,6-dinitrotoluene, and these mixtures preferably have up to 35 percent by weight, based on the total mixture, of 2,6-dinitrotoluene with fractions of from 1 to 5% of vicinal DNT and from 0.5 to 1.5% of 2,5- and 3,5-dinitrotoluene, to the corresponding amines.

The inventive catalysts may be used in a hydrogenation process in which the aromatic nitro compound is used in pure form, as a mixture with the corresponding di- and/or polyamine, as a mixture with the corresponding di- and/or polyamine and water, as a mixture with the corresponding di- and/or polyamine, water and an alcoholic solvent or as a mixture with the corresponding di- and/or polyamine, water, an alcoholic solvent and a catalyst-reactivating additive, and mixtures of two or more of the abovementioned nitro compounds, the corresponding amine compounds, the alcoholic solvent and the catalyst-reactivating additive may also be used.

When a mixture as described above is used, the ratio of amine compound to water is preferably in the range from 10:1 to 1:10, more preferably in the range from 4:1 to 1:1, and the ratio of the amine/water mixture to at least one alcoholic solvent is preferably from 1000:1 to 1:1, more preferably from 50:1 to 5:1.

In order to suppress side reactions, preference is given to conducting the process in such a way that the catalyst is used at its loading limit. This may be controlled, for example, by the amount of the nitro compound metered in, the amount of the catalyst in the reaction mixture, the temperature or the pressure.

The loading limit of the catalyst means the amount of hydrogenatable groups comprising nitrogen and oxygen atoms which may be hydrogenated by the catalyst under given pressure and temperature conditions. The groups comprising nitrogen and oxygen atoms may be not only nitro groups but also nitroso groups and nitrosamine groups.

The catalysts according to the invention are prepared, for example, by initially charging the support and combining it with an aqueous solution of the platinum and nickel salts together with the additional element. The amount of the water used to dissolve the salts is such that a kneadable paste results. Preference is given to using the water in an amount of from 100 to 200% by weight of the support mass. Useful metal salts are in particular nitrates or chlorides, and preference is given to nitrates owing to their low corrosivity. The paste is mixed and then the water is evaporated under reduced pressure and temperatures in the range between 50 and 100° C., for example in a rotary evaporator or an oven. For safety reasons, the evaporation may be effected in a nitrogen stream. When chlorides are used as the metal salts, the metals fixed on the support by reducing with hydrogen. However, this may result in the occurrence of corrosion. Preference is therefore given to fixing the metals under alkaline conditions. This is effected in particular by adding an aqueous solution of alkali metal carbonates and subsequently washing the support to free it of anions. Alternatively, the metals may also be precipitated on the support from a supernatant solution under alkaline conditions, in particular at a pH in the range from 8 to 9. Afterwards, the support is dried, preferably as described above, and reduced with hydrogen. This can for example, in a rotary sphere furnace. Before the catalyst is conditioned, it is passivated, for example under an inert gas such as nitrogen which comprises traces of air, preferably not more than 10% by volume.

The inventive hydrogenation catalysts prepared by this process comprise preferably 1-5% by weight of platinum, 0.3-1.5% by weight of nickel and 0.2-1.0% by weight of the additional element. In particular, they comprise at most 0.9% by weight of base metals.

In another embodiment of the preparation of the inventive hydrogenation catalysts, the catalysts are reduced by adding reducing salts such as ammonium carboxylates, for example ammonium formate. To this end, the support is suspended with water and the solutions of the metal salts is added simultaneously or after the suspension step. The reducing salts are added to this solution and the suspension is heated, for example by boiling under reflux. Subsequently, the catalysts are washed as described above and used in the form of moist pastes.

The inventive hydrogenation catalysts prepared by this process comprise preferably 1-5% by weight of platinum, 0.3-1.5% by weight of nickel and 0.05-0.5% by weight of the additional element. In particular, they comprise at most 0.9% by weight of base metals.

The use of the catalysts according to the invention makes it possible to carry out the hydrogenation of DNT to TDA at temperatures in the range between 120 and 250° C., in particular from 120 to 150° C., at which the selectivity of the reaction deteriorates sharply when conventional catalysts are used. An increase in the reaction temperature is advantageous, since the solubilities of the individual components are higher, and the reaction rate also increases with temperature. The STY (space-time yield) can thus be increased, as long as the energy of reaction can be safely removed.

The invention is illustrated by the examples which follow.

EXAMPLE 1

A Norit® SX+ activated carbon support was initially charged in a dish and platinum(II) nitrate for 3% by weight of platinum, based on the weight of the catalyst, nickel(II) nitrate hexahydrate for 0.9% by weight of nickel and copper (II) nitrate hemipentahydrate for 0.2% by weight of copper, based on the weight of the catalyst, were dissolved in water in an amount of 200% by weight of the amount of the support and added to the support in such a way as to give a kneadable paste. The paste was mixed thoroughly. The water solvent was evaporated in a rotary evaporator with gentle boiling at from 60-70° C. and a pressure of from 0.2 to 0.4 bar. The metals were fixed under alkaline conditions on the support by adding a solution of sodium carbonate in an amount of 16% by weight of the amount of support in 200% by weight of the amount of support of water, and the sample was washed to free it of nitrate. The catalyst obtained in this way was dried at 80° C., before it was reduced in a rotary sphere oven under a hydrogen stream at 400° C. for 4 hours. Before the conditioning, the catalyst was passivated at room temperature in diluted air (5% by volume of air in nitrogen). The catalyst obtained in this way is referred to as catalyst 1.

The catalyst obtained in this way had a content of 2.5% by weight of platinum, 0.75% by weight of nickel and 0.13% by weight of copper.

EXAMPLE 2

The procedure of example 1 was repeated, except that the additional element added was 0.2% by weight of cobalt in the form of cobalt(II) nitrate hexahydrate. The catalyst thus obtained is referred to as catalyst 2. The catalyst thus obtained had a content of 2.9% by weight of platinum, 0.8% by weight of nickel and 0.1% by weight of cobalt.

EXAMPLE 3

The procedure of example 1 was repeated, except that 0.4% by weight of nickel and, as the additional element, 0.25% by weight of zinc in the form of zinc(II) nitrate hexahydrate were added. The catalyst thus obtained is referred to as catalyst 3. The catalyst thus obtained had a content of 2.7% by weight of platinum, 0.39% by weight of nickel and 0.25% by weight of zinc.

EXAMPLE 4

The catalyst used in example 1 was suspended in water to give a 10% suspension. To this end, the metal salts described in example 1 were added in a ratio of 0.7% by weight of nickel and 0.2% by weight of copper and boiled with ammonium formate under reflux for 2 hours. The catalyst thus obtained was washed to free it of nitrate. The catalyst thus obtained is referred to as catalyst 4. The catalyst thus obtained had a content of 2.9% by weight of platinum, 0.65% by weight of nickel and 0.22% by weight of copper.

EXAMPLE 5

The procedure of example 4 was repeated, except that 0.45% by weight of nickel and, as the additional element, 0.2% by weight of cobalt were added. The catalyst thus obtained is referred to as catalyst 5. The catalyst thus obtained had a content of 3.0% by weight of platinum, 0.38% by weight of nickel and 0.09% by weight of cobalt.

EXAMPLE 6

The procedure of example 4 was repeated, except that 0.45% by weight of nickel and, as the additional element, 0.2% by weight of iron were added. The catalyst thus obtained is referred to as catalyst 6. The catalyst thus obtained had a content of 3.0% by weight of platinum, 0.40% by weight of nickel and 0.15% by weight of iron.

EXAMPLE 7

Comparison 1

Commercial nickel catalyst on a $ZrO_2$ support.

EXAMPLE 8

Comparison 2 5% Pd/C

Commercial Pd reference catalyst comprising 5% by weight on activated carbon (50% water-moist).

EXAMPLE 9

Comparison 3

The procedure of example 4 was repeated, except that no nickel salt was added. The catalyst thus obtained is referred to as catalyst 9.

EXAMPLE 10

Comparison 4

The procedure of example 1 was repeated, except that only 1.0% by weight of nickel was added. The catalyst thus obtained is referred to as catalyst 10. The metal content was 2.9% by weight of platinum and 0.97% by weight of nickel.

EXAMPLE 11

Comparison 5

The procedure of example 4 was repeated, except that 1.0% by weight of palladium in the form of palladium(II) nitrate, 15% by weight of nickel and 1.0% by weight of zinc were added. The catalyst thus obtained is referred to as catalyst 11. The metal content was 0.92% by weight of palladium, 13.8% by weight of nickel and 0.96% by weight of zinc.

Hydrogenation of DNT to TDA

The hydrogenation of DNT to TDA was carried out in a 300 ml continuous stirred tank; the catalyst was retained in the reactor mechanically. The catalyst was suspended in water and introduced into the reactor (amount of catalyst from 1 to 2% by weight of the liquid volume of the reactor), brought to a temperature of 125° C. DNT was continuously metered in as a melt, under a hydrogen pressure of 22 bar, in such an amount that a space-time yield of 150-600 $kg_{TDA}/m^3$, h was attained. Samples were analyzed by means of gas chromatography: the TDA yield, formation of high boilers and low boilers was monitored.

The catalysts, their composition and the results can be taken from Table 1.

from the prior art. However, the contents of base metals in catalysts 3, 5-6 is lower than in the comparative catalyst 10; therefore, the workup of this catalyst after use should be more favorable.

We claim:

1. A process for preparing tolylenediamine comprising catalytically hydrogenating dinitrotoluene in the presence of a hydrogenation catalyst wherein said hydrogenation catalyst comprises an active component on a support wherein said active component present consists of a mixture of platinum, nickel and an additional metal selected from the group comprising copper, cobalt, iron, zinc, manganese and chromium, wherein the catalyst comprises 1-5% by weight of platinum, from 0.3 to 1.5% by weight of nickel and 0.05-1.5% by weight of the additional metal, based in each case on the weight of the catalyst, wherein said process is carried out at a pressure in the range of from 10 to 40 bar and a temperature in the range of from 100 to 220° C., and wherein the dinitrotoluene is either used in an environment free of alcohol; or in a mixture wherein the weight ratio of tolylenediamine to water is in the range from 4:1 to 1:1 and the weight ratio of the tolylenediamine/water mixture to at least one alcoholic solvent is from 1000:1 to 5:1.

2. The process according to claim 1, wherein the additional metal is selected from the group comprising copper, cobalt, iron and zinc.

3. The process according to claim 1, wherein the support is selected from the group comprising activated carbon, carbon black, graphite and a metal oxide.

4. The process according to claim 1, wherein the content of base metals in the catalyst is not more than 0.9%.

5. The process according to claim 1, wherein the catalyst is used in an amount of from 0.01 to 5% by weight based on the reaction mixture.

6. The process according to claim 1, wherein the additional metal is copper.

7. The process according to claim 1, wherein the additional metal is cobalt.

8. The process according to claim 1, wherein the additional metal is iron.

| Example | Catalyst | Catalyst - origin or preparation method | Noble metal % | Base metal % | STY ($kg_{TDA}/m^3$, h) | TDA Sel. % |
|---|---|---|---|---|---|---|
| 1 | 2.5%Pt—0.75%Ni—0.13%Cu | 2-stage, ex. 1 | 2.5 | 0.88 | 150-400 | 99.62 |
| 2 | 2.9%Pt—0.80%Ni—0.10%Co | 2-stage, ex. 1 | 2.9 | 0.90 | 200-600 | 99.54 |
| 3 | 2.7%Pt—0.39%Ni—0.25%Zn | 2-stage, ex. 1 | 2.7 | 0.64 | 200-400 | 99.60 |
| 4 | 2.9%Pt—0.65%Ni—0.22%Cu | 1-stage, ex. 4 | 2.9 | 0.87 | 200-600 | 99.56 |
| 5 | 3.0%Pt—0.38%Ni—0.09%Co | 1-stage, ex. 4 | 3.0 | 0.47 | 400-600 | 99.53 |
| 6 | 3.0%Pt—0.40%Ni—0.15%Fe | 1-stage, ex. 4 | 3.0 | 0.55 | 400-600 | 99.53 |
| 7 | 65%Ni/ZrO2 | commercial | 0.0 | 65.00 | 150-600 | 99.30 |
| 8 | 5%Pd | commercial | 5.0 | 0 | 150-600 | approx. 95 |
| 9 | 3%Pt | 1-stage, ex. 4 | 3.0 | 0 | 150-600 | 99.00 |
| 10 | 2.9%Pt—0.97%Ni | 2-stage, ex. 1 | 2.9 | 0.97 | 400-600 | 99.50 |
| 11 | 0.92%Pd—13.8%Ni—0.96%Zn | 1-stage, ex. 4 | 0.9 | 15.68 | 150-600 | 99.21 |

The examples show that the monometallic catalysts (7-9) give rise to yields which are distinctly inferior to those of the inventive catalysts (1-6). With the trimetallic catalysts 1-3 which are prepared in two stages according to example 1, it is possible to achieve a high TDA selectivity which is superior to the bimetallic Pd—Ni catalyst 10 and also to the trimetallic Pd—Ni—Zn catalyst 11. With the trimetallic catalysts 4-6 which have been prepared in one stage, it was possible to achieve TDA selectivities which are comparable with those from the bimetallic Pt—Ni catalysts (10) known 9. The process according to claim 1, wherein the additional metal is zinc.

10. The process according to claim 1, wherein the support is activated carbon.

11. The process according to claim 1, wherein the support is carbon black.

12. The process according to claim 1, wherein the support is graphite.

13. The process according to claim 1, wherein the support is a metal oxide.

\* \* \* \* \*

UNITED STATES PATENT AND TRADEMARK OFFICE
CERTIFICATE OF CORRECTION

PATENT NO. : 9,505,705 B2
APPLICATION NO. : 12/065285
DATED : November 29, 2016
INVENTOR(S) : Petr Kubanek et al.

It is certified that error appears in the above-identified patent and that said Letters Patent is hereby corrected as shown below:

On the Title Page

Item (73), the Assignee's name is misspelled. Item (73) should read:
--(73) Assignee: BASF AKTIENGESELLSCHAFT, Ludwigshafen, (DE)--

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*